US006808723B2

United States Patent
Hakkinen et al.

(10) Patent No.: US 6,808,723 B2
(45) Date of Patent: Oct. 26, 2004

(54) GASTRIC ACID SECRETION

(75) Inventors: John Hakkinen, North Stonington, CT (US); Roelof Marthinus Horak, Pretoria (ZA); Vinesh Maharaj, Pretoria (ZA)

(73) Assignee: Phytopharm PLC, Godmanchester (GB)

(*) Notice: Subject to any disclaimer, the term of this patent is extended or adjusted under 35 U.S.C. 154(b) by 66 days.

(21) Appl. No.: 10/171,640

(22) Filed: Jun. 17, 2002

(65) Prior Publication Data

US 2002/0192306 A1 Dec. 19, 2002

Related U.S. Application Data

(62) Division of application No. 09/691,582, filed on Oct. 18, 2000, now Pat. No. 6,488,967.

(30) Foreign Application Priority Data

Oct. 27, 1999 (GB) .............................................. 9925457

(51) Int. Cl.[7] ............................. A61K 35/78; C07J 5/00

(52) U.S. Cl. ............................................ 424/725; 536/5
(58) Field of Search ............................... 424/725; 536/5

(56) References Cited

U.S. PATENT DOCUMENTS 4,806,549 A * 2/1989 Ife et al.

FOREIGN PATENT DOCUMENTS

WO        WO 98/46243        10/1998

* cited by examiner

*Primary Examiner*—Christopher R. Tate
*Assistant Examiner*—Michele Flood
(74) *Attorney, Agent, or Firm*—Morgan, Lewis & Bockius LLP

(57) ABSTRACT

The present application relates to the reduction of gastric acid secretion in animals including humans; to methods of treating conditions or disorders associated with or exacerbated by gastric acid secretion; to pharmaceutical compositions useful in carrying out such methods; and to the use of certain extracts and compounds in the treatment of human and non-human animals, generally mammals.

3 Claims, No Drawings

GASTRIC ACID SECRETION

This application is a Divisional of copending application Ser. No. 09/691,582, filed Oct. 18, 2000, now allowed as U.S. Pat. No. 6,488,967, which claims priority from co-pending Application No. GB9925457.5, filed Oct. 27, 1999.

This invention relates to the reduction of gastric acid secretion in animals including humans; to methods of treating conditions or disorders associated with or exacerbated by gastric acid secretion; to pharmaceutical compositions useful in carrying out such methods; and to the use of certain extracts and compounds in the treatment of human and non-human animals, generally mammals.

Excessive secretion of gastric acid can lead to or aggravate a number of disorders, for example oesophageal reflux disease, e.g. reflux oesaphagitis, haemorrhage in and benign ulceration of the stomach and duodenum (including those complicating NSAID therapy). These conditions tend to be more problematical in obese patients and patients with hiatus hernia. The present invention is directed, in part, to the treatment of these conditions and of ancillary indications, e.g. to provide relief of reflux-like symptoms (e.g. heartburn) and/or ulcer-like symptoms (e.g. epigastric pain) associated with acid-related dyspepsia; for general dyspeptic symptoms; and for prophylaxis of acid aspiration.

Non-steroidal anti-inflammatory drugs (NSAIDs), e.g. aspirin (acetylsalicylic acid), are well-known and widely used for their anti-inflammatory and antipyretic properties. A major side effect is their tendency to damage the wall of the stomach; this adverse property is acid-dependent and is generic to the NSAIDs. The present invention is also concerned with means for mitigating these adverse effects.

It is known from International Patent Publication No. WO 98/46243 that extracts of certain plants of the genus *Trichocaulon* or *Hoodia* possess appetite suppressant properties. This document also discloses certain specific compounds which possess appetite suppressant activity. Among these is the compound 3-O-[-β-D-thevetopyranosyl-(1→4)-β-D-cymaropyranosyl-(1→4)-β-D-cymaropyranosyl]-12β-O-tigloyloxy-14-hydroxy-14β-pregn-5-en-20-one; the structural formula of this compound is given as formula (1) in WO 98/46243. We have found that this compound is effective in reducing the secretion of gastric acid; accordingly, the compound finds application in the present invention. Derivatives of this compound are also effective in the present invention; such derivatives have the general formula

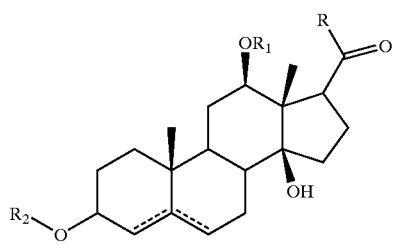

in which R=alkyl;
R$_1$=H, alkyl, tigloyl, benzoyl, or any other organic ester group;
R$_2$=H, or one or more 6-deoxy carbohydrate, or one or more 2,6-dideoxy carbohydrates, or glucose molecules, or combinations thereof;
in which the acyl group R—(C=O)— group can be in the reduced form R—(C—OH)—;

and in which the dashed lines indicate the optional presence of a double bond in the C4–C5 or C5–C6 positions.

Thus, according to a first aspect of the present invention, there is provided a method of reducing gastric acid secretion in an animal, which comprises administering to said animal:
(a) an extract of a plant of the genus *Hoodia* or *Trichocaulon*; or
(b) a compound of the formula

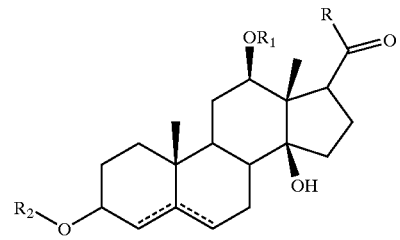

wherein: R=an alkyl group containing from one to four carbon atoms;
R$_1$=H, an alkyl group containing from one to four carbon atoms, or an organic ester group;
R$_2$=H, or one or more 6-deoxy carbohydrates, or one or more 2,6-dideoxy carbohydrates, or glucose, or a combination thereof;
and in which the dashed bonds indicate the optional presence of a double bond at the C4–C5 position or the C5–C6 position.

Advantageously, when R$_1$ is an organic ester group it is tigloyl, benzoyl or anthraniloyl. In a preferred embodiment, R is an alkyl group having from one to four carbon atoms, R$_1$ is tigloyl or anthraniloyl; and a double bond is present in the C5–C6 position.

Advantageously, R$_2$ is trisaccharide group. The component sugars of said trisaccharide group are preferably 6-deoxy and/or 2,6-dideoxy hexoses. In some embodiments, the terminal hexose moiety is thevetosyl.

The compound may be 3-O-[-β-D-thevetopyranosyl-(1→4)-β-D-cymaropyranosyl-(1→4)-β-D-cymaropyranosyl]-12β-O-tigloyloxy-14-hydroxy-14β-pregn-5-en-20-one.

According to a second aspect of the present invention, there is provided a method of treating a disorder of the alimentary system in an animal, which comprises administering to the animal
(a) an extract of a plant of the genus *Hoodia* or *Trichocaulon*; or
(b) a compound of the formula

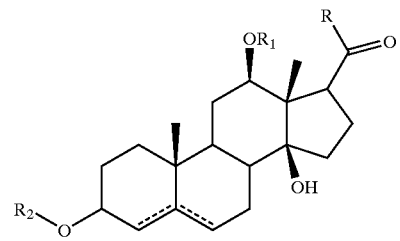

wherein: R=an alkyl group containing from one to four carbon atoms;
R$_1$=H, an alkyl group containing from one to four carbon atoms, or an organic ester group;
R$_2$=H, or one or more 6-deoxy carbohydrates, or one or more 2,6-dideoxy carbohydrates, or glucose, or a combination thereof;

and in which the dashed bonds indicate the optional presence of a double bond at the C4–C5 position or the C5–C6 position.

This method can conveniently be used in the treatment of reflux oesophagitis. It is also expected to find application in the treatment of epigastric pain; dyspepsia; gastric ulceration; and acid aspiration.

According to a third aspect of the present invention, there is provided a method of protecting a mammalian gastrointestinal tract from damage caused by a non-steroidal anti-inflammatory drug, which comprises administering an effective amount of:

(a) an extract of a plant of the genus *Hoodia* or *Trichocaulon*; or
(b) a compound of the formula

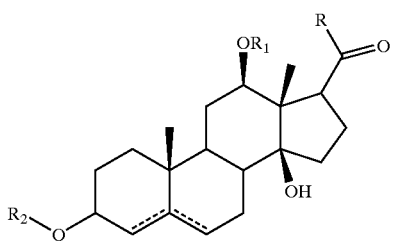

wherein: R=an alkyl group containing from one to four carbon atoms;
$R_1$=H, an alkyl group containing from one to four carbon atoms, or an organic ester group;
$R_2$=H, or one or more 6-deoxy carbohydrates, or one or more 2,6-dideoxy carbohydrates, or glucose, or a combination thereof;
and in which the dashed bonds indicate the optional presence of a double bond at the C4–C5 position or the C5–C6 position.

According to a fourth aspect, the present invention provides a method of protecting a mammalian gastro-intestinal tract from damage caused by a non-steroidal anti-inflammatory drug, which comprises administering an effective amount of [3-O-[-β-D-thevetopyranosyl-(1→4)-β-D-cymaropyranosyl-(1→4)-β-D-cymaropyranosyl]-12β-O-tigloyloxy-14-hydroxy-14β-pregn-5-en-20-one or a derivative thereof.

When a plant extract is used in the invention, it is presently preferred to use an extract from the plant *Hoodia gordonii* or *Hoodia currori*. Advantageously, the said extract comprises spray-dried sap of the plant *Hoodia gordonii*.

The methods in accordance with this invention are applicable to the treatment of humans.

According to a fifth aspect of the present invention, there is provided a pharmaceutical composition comprising a non-steroidal anti-inflammatory drug and a compound of the formula

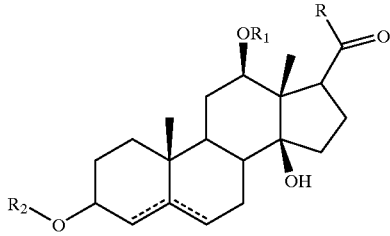

wherein: R=an alkyl group containing from one to four carbon atoms;

$R_1$=H, an alkyl group containing from one to four carbon atoms, or an organic ester group;
$R_2$=H, or one or more 6-deoxy carbohydrates, or one or more 2,6-dideoxy carbohydrates, or glucose, or a combination thereof;
in which the acyl group R—(C=O)— group can be in the reduced form R—(C—OH)—;
and in which the dashed bonds indicate the optional presence of a double bond at the C4–C5 position or the C5–C6 position.

A preferred pharmaceutical composition of this type utilises the compound 3-O-[-β-D-thevetopyranosyl-(1→4)-β-D-cymaropyranosyl-(1→4)-β-D-cymaropyranosyl]-12β-tigloyloxy-14-hydroxy-14β-pregn-5-en-20-one or a derivative thereof. The pharmaceutical compositions of this invention are conveniently prepared in unit dosage form; they may also include a pharmaceutically acceptable diluent, excipient or carrier.

According to a sixth aspect of the present invention, there is provided method of treating a condition or disorder caused by or exacerbated by gastric acid secretion in an animal, which comprises administering to the animal a pharmaceutical composition as just defined. The animal may be a human.

According to a seventh aspect, the present invention provides the use of a compound of the formula

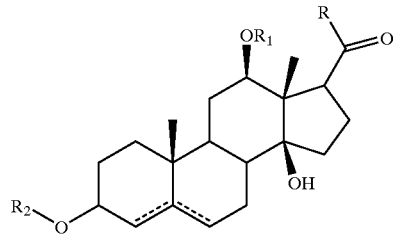

wherein: R=an alkyl group containing from one to four carbon atoms;
$R_1$=H, an alkyl group containing from one to four carbon atoms, or an organic ester group;
$R_2$=H, or one or more 6-deoxy carbohydrates, or one or more 2,6-dideoxy carbohydrates, or glucose, or a combination thereof;
in which the acyl group R—(C=O)— group can be in the reduced form R—(C—OH)—;
and in which the dashed bonds indicate the optional presence of a double bond at the C4–C5 position or the C5–C6 position,
in the manufacture of a medicament for the treatment of a disorder caused by or exacerbated by gastric acid secretion. For such use, the compound may be 3-O-[-β-D-thevetopyranosyl-(1→4)-β-D-cymaropyranosyl-(1→4)-β-D-cymaropyranosyl]-12β-O-tigloyloxy-14-hydroxy-14β-pregn-5-en-20-one or a derivative thereof.

According to an eighth aspect, the present invention provides the use of an extract of a plant of the genus *Hoodia* or *Trichocaulon* in the manufacture of a medicament for the treatment of conditions and disorders caused by or exacerbated by gastric acid secretion. The condition or disorder for which the medicament is intended may be reflux oesophagitis; or gastric or duodenal ulceration; gastro-duodenal erosion; or epigastric pain.

According to a ninth aspect, the present invention provides the use of an extract of a plant of the genus *Hoodia* or *Trichocaulon* in the manufacture of a medicament for the treatment of conditions and disorders caused by or exacerbated by gastric acid secretion.

According to a tenth aspect, the present invention provides the use of an extract of a plant of the genus *Hoodia* or *Trichocaulon* in the manufacture of a medicament for the treatment of reflux oesophagitis.

According to an eleventh aspect, the present invention provides the use of an extract of a plant of the genus *Hoodia* or *Trichocaulon* in the manufacture of a medicament for preventing or reducing gastric damage associated with use of a non-steroidal anti-inflammatory drug.

According to a twelfth aspect, the present invention provides the use of 3-O-[-β-D-thevetopyranosyl-(1→4)-β-D-cymaropyranosyl-(1→4)-β-D-cymaropyranosyl]-12β-O-tigloyloxy-14-hydroxy-14β-pregn-5-en-20-one or a derivative thereof in the manufacture of a medicament for preventing or reducing gastric damage associated with use of a non-steroidal anti-inflammatory drug.

The extracts of a plant of the genus *Hoodia* or *Trichocaulon* useful in the present invention may generally be prepared by extracting sap from the plant and then spray-drying the sap. Alternatively, solvent extraction procedures may be employed. In either case, fractionation of the initial extract, e.g. by column chromatography, may follow in order to generate am extract with enhanced activity.

The extract may be prepared from plant material such as the stems and roots of plants of the genus *Hoodia* or the genus *Trichocaulon*; these genera include succulent plants which grow in the arid regions of southern Africa.

methylene chloride extract and a water extract. The methylene chloride extract may have the solvent removed by, for example, a rotary evaporator and the resultant extract may be further purified by way of a methanol/hexane extraction. The methanol/hexane extraction product may then be separated to yield a methanol extract and a hexane extract. The methanol extract may be evaporated to remove the solvent in order to yield a partially purified active extract.

The partially purified active extract may be dissolved in methanol, and may be further fractionated by column chromatography, employing silica gel as an adsorption medium and a chloroform/30% methanol mixture as eluent. A plurality of different fractions may be obtained, and each may be evaluated, by suitable bioassaying procedures, to determine their activity. High activity fractions may be further fractionated, e.g. by column chromatography using silica gel as an adsorption medium and a 9:1 chloroform:methanol eluent. This process may be repeated using silica gel as an adsorption medium and a 9:1 ethylacetate:hexane eluent.

Alternatively, the plant product may be compressed or macerated to extract sap therefrom, then filtered to remove unwanted solids and freeze-dried. The freeze-dried sap product may then be further purified, if desired, for example using chromatographic fractionation such as described above.

The derivatives of 3-O-[-β-D-thevetopyranosyl-(1→4)-β-D-cymaropyranosyl-(1→4)-β-D-cymaropyranosyl]-12β-O-tigloyloxy-14-hydroxy-14β-pregn-5-en-20-one which find use in this invention are advantageously of the formula:

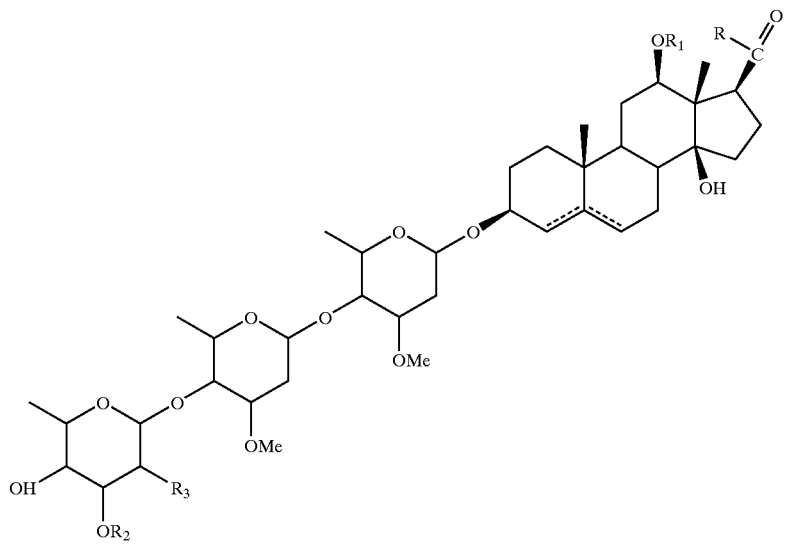

Advantageously, the plant extract is obtained from one of the following species: *Trichocaulon piliferum; Trichocaulon officinale; Hoodia currorii; Hoodia gordonii;* and *Hoodia lugardii.*

The plant material may be homogenised in the presence of a suitable solvent, e.g. a methanol/methylene chloride solvent, by means of a device such as a Waring blender. The extraction solution may then be separated from residual plant material by an appropriate separation procedure such as, for example, filtration or centrifugation. The solvent may, for example, be removed by means of a rotary evaporator, preferably in a water bath at a temperature of 60° C. The separated crude extract may then be further extracted with methylene chloride and water before being separated into a in which R=alkyl;

$R_1$=H, alkyl, tigloyl, benzoyl, or any other organic ester group;

$R_2$=H or alkyl;

$R_3$=H or OH;

in which the acyl group R—(C=C)— group can be in the reduced form R—(C—OH)—;

and in which the dashed lines indicate the optional presence of a further bond in the C4–C5 or C5–C6 positions;

The invention will be illustrated by the following Examples:

EXAMPLE 1

The ability of the compound 3-O-[-β-D-thevetopyranosyl-(1→4)-β-D-cymaropyranosyl-(1→4)-β-D-cymaropyranosyl]-12β-O-tigloyloxy-14-hydroxy-14β-pregn-5-en-20-one hereinafter referred to as P57AS3—to prevent aspirin-induced damage to the stomach was investigated in the rat. Three groups each containing eight rats were given aspirin in 0.5% CMC orally at a dose of about 600 mg/kg (1.0 ml of 60 mg/ml) The first group (the control group) was additionally given 0.5% CMC. The second group was given compound P57AS3 at a dose rate of 100 mg/kg; and the third group (comparative group) was given cimetidine at a dose rate of 20 mg/kg.

After 5 hours, the animals' stomachs were visually inspected for damage. Damage was assessed on a scale in which each small haemorrhage scored one point; each large haemorrhage scored two points; each small ulcer scored three points; and each large ulcer scored four points. The results obtained were as follows:

TABLE 1

| Oral treatment | Dose (mg/kg) | Rat no. | Gastric damage score |
|---|---|---|---|
| Vehicle (0.5% CMC) | – | 1 | 10 |
| | | 2 | 10 |
| | | 3 | 16 |
| | | 4 | 8 |
| | | 5 | 5 |
| | | 6 | 3 |
| | | 7 | 1 |
| | | 8 | 6 |
| | | Mean | 7.38 |
| P57AS3 | 100 | 9 | 0 |
| | | 10 | 0 |
| | | 11 | 3 |
| | | 12 | 0 |
| | | 13 | 0 |
| | | 14 | 0 |
| | | 15 | 2 |
| | | 16 | 0 |
| | | Mean | 0.63 |
| Cimetidine | 20 | 17 | 0 |
| | | 18 | 0 |
| | | 19 | 4 |
| | | 20 | 0 |
| | | 21 | 0 |
| | | 22 | 0 |
| | | 23 | 0 |
| | | 24 | 0 |
| | | Mean | 0.50 |

These results show that compound P57AS3 gave an average reduction in gastric damage of 91.5% compared to 93.2% for cimetidine. In both cases, the statistical significance of the difference from the control group was $P<0.01$.

EXAMPLE 2

The effect of both the spray dried extract (sap from *Hoodia gordonii*)—referred to hereinafter as P57SD—and the purified compound P57AS3 were examined for effects on gastric acid secretion in the pylorus-ligated rat. Male Sprague-Dawley derived CD rats, 175–230 g, were used. On the day before the test, rats were outfitted with stainless steel tail cups to prevent coprophagy, housed individually with water allowed ad lib, and fasted overnight (18 hr). In one test the spray dried sap P57SD (5 or 50 mg/kg), or cimetidine (10 mg/kg) or vehicle (water) was orally administered to the rats immediately before fasting. Water was removed 30 minutes prior to ligation on the morning of the test. Under isoflurane anesthesia, a midline celiotomy was performed, and the pylorus of each rat was ligated with 4-0 silk.

In a second experiment, purified compound P57AS3 was administered intraduodenally (i.d.) at 1 or 10 mg/kg at the time of the pylorus ligation. In this experiment with intraduodenal administration of P57AS3, vehicle (DMSO), cimetidine (10 mg/kg) or P57AS3 (1 or 10 mg/kg) was administered immediately after ligation. The incisions were then closed with staples. In the experiments with subcutaneous administration of P57, vehicle (DMSO), cimetidine (10 mg/kg) or P57, 10 or 30 mg/kg were injected subcutaneously in the nape of the neck immediately after the incisions were closed. Two hours after ligation, the rats were killed, the contents of each stomach collected and cleaned by centrifugation (30 minutes at 2000×g), and the volume of gastric fluid in each stomach was determined. Using a Radiometer pH meter and autotitrator, the pH and acid concentration of each gastric sample was determined by titration to pH 7 with 0.1N NaOH. Results are expressed as μeq/hr/100 g (body weight) and % vehicle control.

In the first experiment, gastric acid output was determined 18 hours after rats were orally administered the spray dried sap P57SD. Results showed that the 5 mg/kg dose of P57SD was without effect, but the 50 mg/kg dose-inhibited gastric acid secretion by 40%. (Table 2). In a second experiment, the purified compound P57AS3 was administered intraduodenally (i.d.) at 1 or 10 mg/kg at the time of the pylorus ligation. The 10 mg/kg i.d. dose of P57AS3 decreased acid secretion by 88%, but the 1 mg/kg i.d. dose had no effect (Table 2). Experiments were then conducted to determine if systemically administered P57AS3 would also inhibit gastric acid secretion. P57AS3 was administered subcutaneously at the time of ligation in 3 experiments using 10 mg/kg and in one experiment using 30 mg/kg. In one of the experiments with 10 mg/kg, P57AS3 produced a significant decrease in gastric acid secretion, but in the other 2 experiments with 10 mg/kg and the one experiment with 30 mg/kg there was a trend toward decreased acid output but the amount of acid secretion was not significantly different from vehicle-treated controls (Table 2). In each pylorus ligation experiment, gastric acid secretion was significantly reduced (range 36% to 83% inhibition) in a group of rats treated with cimetidine (10 mg/kg), which was included as a positive control.

TABLE 2

Effect of P57 on gastric acid secretion in the pylorus-ligated rat

| Exp. | Active | Dose (mg/kg) | Route | Acid Output % Control mean ± sd |
|---|---|---|---|---|
| I | P57SD | 5 | po | 85.4 ± 34.5 |
| | | 50 | po | *60.0 ± 21.7 |
| II | P57AS3 | 1 | id | 109.0 ± 37.8 |
| | | 10 | id | *12.4 ± 1.1 |
| III | P57AS3 | 10 | sc | 48.9 ± 29.2 |
| IV | P57AS3 | 10 | sc | 74.0 ± 38.0 |
| V | P57AS3 | 10 | sc | *57.1 ± 19.8 |
| VI | P57AS3 | 30 | sc | 63.7 ± 17.3 |

*significantly different from vehicle group, $p \leq 0.05$

Summary of Results
In Vitro Studies

Purified P57AS3 was examined for binding affinity to a variety of receptors, channels, and uptake sites in vitro. At a concentration of 10 μM, In isolated tissue studies, P57AS3 at concentrations ≦10 μM had no effect on the rate of spontaneously beating guinea pig right atria or on the force of contraction of electrically stimulated left atria. At concentrations of 1 μM and higher, P57AS3 produced intermittent and transient elevations in the basal tension of electrically stimulated left atria. P57AS3 had no effect on resting tension of isolated guinea pig gallbladder, ileum or trachea, or on CCK octapeptide-induced contractions of the gallbladder (CCK-A receptor mediated), histamine induced contractions of the guinea pig ileum ($H_1$ receptor mediated), or acetylcholine-induced contractions of the guinea pig ileum ($M_3$ receptor mediated). At concentrations ≧1 μM, P57AS3 noncompetitively inhibited carbachol-induced contractions of the guinea pig trachea ($M_3$ receptor mediated).

In Vivo Studies

The spray dried form of P57 was examined for effects on gastrointestinal motility and both the spray dried and purified forms were examined for effects on gastric acid secretion in the rat. At a dose of 5 mg/kg p.o., spray dried P57 had no effect on gastrointestinal transit or on gastric acid secretion. However, a 50 mg/kg dose of spray dried P57 inhibited gastric emptying by 26% and acid output by 40%. Following intraduodenal (id) administration in the rat, purified P57AS3 had no effect on gastric acid secretion at a dose of 1 mg/kg, but a 10 mg/kg dose decreased acid output by 88%. In 2 of 3 experiments at a dose of 10 mg/kg and in one experiment at a dose of 30 mg/kg, subcutaneously (sc) administered purified P57AS3 had no effect on gastric acid output, but in 1 of 3 experiments the 10 mg/kg sc dose reduced gastric acid secretion by 43%.

References

1. Hill S J, and Young J M. Characterization of [3H] mepyramine binding to the longitudinal muscle of guinea pig small intestine. Mol Pharmacol 1981; 19:379–387.
2. Eltze M, Mutschler E, and Lambrecht G. Affinity profiles of pizotifen, ketotifen and other tricyclic antimuscarinics at muscarinic receptor subtypes M1, M2 and M3. Eur J Pharmacol 1992; 211:283–293.
3. Bishop L A, Gerskowitch V P, Hull R A, Shankley N P, Black J W. Combined dose-ratio analysis of cholecystokinin receptor antagonists, devazepide, lorglumide and loxiglumide in the guinea pig gallbladder. Br J Pharmacol 1992; 106:61–66.

What is claimed is:

1. A pharmaceutical composition comprising a non-steroidal anti-inflammatory drug and a compound of the formula

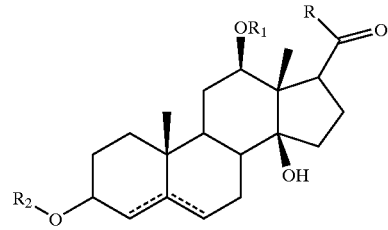

wherein: R=an alkyl group containing from one to four carbon atoms;

$R_1$=H, an alkyl group containing from one to four carbon atoms, or an organic ester group;

$R_2$=H, or one or more 6-deoxy carbohydrates, or one or more 2,6-dideoxy carbohydrates, or glucose, or a combination thereof;

and in which the dashed bonds indicate the optional presence of a double bond at the C4–C5 position or the C5–C6 position.

2. A pharmaceutical composition as claimed in claim 1, wherein said compound is 3-O-[-β-D-thevetopyranosyl-(1→4)-β-D-cymaropyranosyl]-12β-O-tigloyloxy-14-hydroxy-14β-pregn-5-en-20-one or a derivative thereof.

3. A pharmaceutical composition as claimed in claim 1, which is prepared in unit dosage form.

* * * * *